US006380358B1

(12) United States Patent
Goodman et al.

(10) Patent No.: US 6,380,358 B1
(45) Date of Patent: Apr. 30, 2002

(54) GUANIDINYLATION REAGENTS

(75) Inventors: Murray Goodman, La Jolla; Konrad Feichtinger; Todd T. Romoff, both of San Diego, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/452,895

(22) Filed: Dec. 1, 1999

Related U.S. Application Data

(62) Division of application No. 08/861,942, filed on May 22, 1997, now Pat. No. 6,072,075.

(51) Int. Cl.$^7$ .................... C07C 277/08; C07C 279/24; C07K 1/04; C07K 1/05
(52) U.S. Cl. .................. 530/334; 530/329; 530/330; 530/333; 530/335; 530/336; 530/337; 530/338; 530/343; 560/13; 560/25; 560/148; 560/158; 544/400; 548/561; 548/567
(58) Field of Search .................... 530/329, 330, 530/333, 334, 335, 336, 337, 338, 343; 560/13, 25, 148, 158; 544/400; 548/561, 567

(56) References Cited

U.S. PATENT DOCUMENTS

| | | | |
|---|---|---|---|
| 1,677,235 A | 7/1928 | Heuser | 525/332.5 |
| 1,681,806 A | 8/1928 | Heuser | 525/332.5 |
| 1,795,738 A | 3/1931 | Schotte | 564/238 |
| 1,953,494 A | 4/1934 | Meis | 260/125 |
| 2,898,369 A | 8/1959 | Cain | 260/501 |
| 3,062,804 A | 11/1962 | Albertson | 260/112 |
| 3,062,805 A | 11/1962 | Albertson et al. | 260/112 |
| 3,117,994 A | 1/1964 | McKay et al. | 260/564 |
| 3,301,755 A | 1/1967 | Mull | 167/65 |
| 3,320,229 A | 5/1967 | Szabo et al. | 260/96.5 |
| 3,388,113 A | 6/1968 | Guttmann et al. | 260/112.5 |
| 3,479,437 A | 11/1969 | Szabo et al. | 424/304 |
| 3,551,490 A | 12/1970 | Flynn et al. | 260/564 |
| 3,609,164 A | 9/1971 | Miyoshi et al. | 260/309 |
| 3,646,029 A | 2/1972 | Mullins et al. | 260/268 R |
| 3,896,160 A | 7/1975 | Gáetzi | 260/482 C |
| 3,978,035 A | 8/1976 | Wünsch et al. | 260/112.5 R |
| 4,083,848 A | 4/1978 | Itoh et al. | 260/239.1 |
| 4,358,613 A | 11/1982 | Mark | 564/238 |
| 4,471,137 A | 9/1984 | Barton et al. | 564/240 |
| 4,956,388 A | 9/1990 | Robertson et al. | 514/651 |
| 5,246,810 A | 9/1993 | Hagiwara et al. | 430/110 |
| 5,262,568 A | 11/1993 | Weber et al. | 564/238 |

FOREIGN PATENT DOCUMENTS

| DE | 2 544 348 A | 7/1977 |
|---|---|---|
| EP | 0 646 573 A | 5/1995 |

OTHER PUBLICATIONS

Beck–Stickinger, A. et al. (1991) Sulfonation of arginine residues as side reaction in Fmoc–peptide synthesis. Int J Peptide Protein Res 38:25–31.
Berlinck, R.G.S. (1995) Some aspects of guanidine secondary metabolites. Progress in the Chemistry of Organic Natural Products. 66:119.
Berlinck, R.G.S. (1996) Natural guanidine derivatives. Nat Prod Reports 13(5):377–409.
Bernatowicz, M. et al. (1992) 1H–pyrazole–1–carboxamidine hydrochloride: and attractive reagent for guanylation of amines and its application to peptide synthesis. J Org Chem 57:2497–2502.
Bernatowicz, M. et al. (1993) Urethane protected derivative of 1–guanylpyrazole for the mild and efficient preparation of guanidines. Tetrahedron Letters 3389–3392.
Bodanszky, M. (1984) Principles of peptide synthesis Chap. 111 Sec. C, Springer–Verlag, New York.
Burgess, K., et al. (1994) Asymmetric synthesis of protected derivatives of carnosadine and stereoisomers as confromationally constrained surrogates for arginine. J Org Chem 59:2179–2185.
Dodd, D. et al. (1994) Conversion of alcohols to protected guanidines using the Mitsunobu protocol, Tetrahedron Letters 35(7):977–980.
Drake, B. et al. (1994) A convenient preparation of monosubstituted N,N'–di(boc)–protected guanidines. Synthesis 579–582.
Ferrario, F. et al. (1991) Multigram synthesis of Ng–methyl–(L)–arginine and its analytical characterization. Synthetic Communications 21(1):99–105.
Fischer, P. et al. (1992) Application of arylsulphonyl side–chain protected arginines in solid–phase peptide synthesis based on 9–fluorenylmethoxycarbonyl amino protecting strategy. Int J Peptide Protein Res 40:19–24.
Fujino, M. et al. (1981) Further studies on the use of multi–substituted benzenesulfonyl groups for protection of the guanidino function of arginine. Chem Pharm Bull 29(10):2825:2831.
Fuller, W.D. et al. (1996) Urethane–protected α–amino acid N–carboxyanhydrides and peptide synthesis. Biopolymers (Peptide Science) 40:183–205.
Geiger, R. et al. (1981) The peptides, vol. 3. Amine protecting groups. ISBN 0–12–304203–8.
Jaeger, E. et al. (1993) O–sulfonierung von serin und theonin wahrend der abspaltung der pmc–und mtr–schutzgruppen von arginiresten bei fmon–festphasen–synthesen. Biol Chem Hoppe–Seyler 374:349–362.

(List continued on next page.)

*Primary Examiner*—Peter O'Sullivan
(74) *Attorney, Agent, or Firm*—Gray Cary Ware & Freidenrich LLP; Lisa A. Haile

(57) ABSTRACT

Trisubstituted N-protected guanidines and methods for use as guanidinylating reagents to yield N-protected guanidine derivatives.

9 Claims, 2 Drawing Sheets

OTHER PUBLICATIONS

Jenny, T.F. et al. (1991) Carbocyclic analogs of nucleosides via modified Mitsunobu reactions. Tetrahedron Letters. 32(48):7029–7032.

Katritzky, A. et al. (1995) Benzotriazole–1–carboxamidinium tosylate: and alternative method for the conversion of amines to guanidines. Synthetic Communications 25(8):1173–1186.

Kim, K. et al. (1993) Improved method for the preparation of guanidines. Tetrahedron Letters 34(48):7677–7680.

Ko, S. et al (1995) An efficient synthesis of internal guanidines. Synlett 815–816.

Mitsunobu, O. (1981) The use of diethyl azodicarboxylate and triphenylphosphine in synthesis and transformation of natural products. Georg Thieme Verlag 1–28.

Moormann, A. (1993) Reductive amination of piperidines with aldehydes using borane–pyridine. Synthetic communications 23(6):789–795.

Poss, M. et al. (1992) A mild and efficient method for the preparation of guanidines. Tetrahedron Letters 5933–5936.

Ramadas, K. et al. (1995) An expedient synthesis of substituted guanidines. Tetrahedron Letters 36(16):2841–2844.

Ramaga, R. et al. (1991) An acid labile arginine derivative for peptide synthesis: Ng–2,2,5,7,8–pentamethylchroman–6–sulphonyl–L–arginine. Tetrahedron Letters 47(32):6353–6370.

Tian, Z. et al. (1992) Synthesis of optically pure $C^{\alpha}$–methyl–arginine. Int J Peptide Protein Res 40:119–126.

Tian, Z et al. (1991) Guanidination of a peptide side chain amino group on a solid support. Int J Peptide Protein Res 37:425–429.

Verdini, A. et al. (1992) A facile preparation of Fmoc–Arg . . . Tetrahedron Letters 33(43):6541–6542.

Webb, T. et al. (1991) Conformationally restricted arginine analogoues. J Org Chem 56:3009–3016.

Wu, Y. et al. (1993) An efficient method for the preparation of $\omega,\omega'$–bis–urethane protected arginine derivatives. Synthetic Communications 23(21):3055–3060.

Wünsch, E. (1974) methoden der Org. Chem (Houben–Weyl) (Wünsch, E., ed.), Stuttgart: Thieme 15/1:46.

Zhang, W. et al. (1994) A highly efficient preparation of $N^G$–methyl–L–arginine and $N^G$–methyl–d–arginine. Synthetic Comm 24(19):2789–2792.

GUANIDINYLATION REAGENTS

This is a division of application Ser. No. 08/861,942, filed May 22, 1997 now U.S. Pat. No. 6,072,075.

FIELD OF THE INVENTION

The invention relates to reagents and methods for the synthesis of organic molecules containing a guanidine group. It relates particularly to reagents useful for introducing a protected guanidine group into a molecule.

BACKGROUND OF THE INVENTION

Many natural compounds that bear a guanidine function have biological activity that make them useful as pharmaceuticals. Among these compounds are antimicrobials, antifungals, antivirals, neurotoxins, hormones, and agents that act as agonists or antagonists to biological signals. A review of these natural products is presented in Progress in the Chemistry of Organic Natural Products (1995) 66:119 and Berlinck, R. G. S. (1996) Nat. Prod. Reports 13(5) :377–409. Much effort has been directed to developing routes for preparing these compounds or their analogues synthetically.

Guanidine-containing bioactive molecules, particularly the analogs or derivatives of the natural products, are now significant targets for drug design and discovery. The guanidine moiety in the bioactive compound frequently occurs in arginine-containing polypeptide chains which may comprise the entire biomolecule or exist as an incorporated moiety. Arginine, together with lysine, another amino acid with a positively charged side chain, plays an important role in biologically active proteins and peptides. Various arginine analogues and derivatives have been synthesized and incorporated into peptides and peptidomimetics to study the structure-activity relationships of arginine-containing molecules. These residues are frequently the critical amino acid residues in peptidomimetics.

A completely satisfactory guanidinylating reagent has not yet been achieved. More effective guanidinylation reagents are useful in improving the synthesis of arginine analogues and other guanidine-containing molecules.

BRIEF DESCRIPTION OF THE FIGURES

FIG. 1: X-ray structure of

DETAILED DESCRIPTION OF THE PREFERRED EMBODIMENT

Definitions

Figure 1:
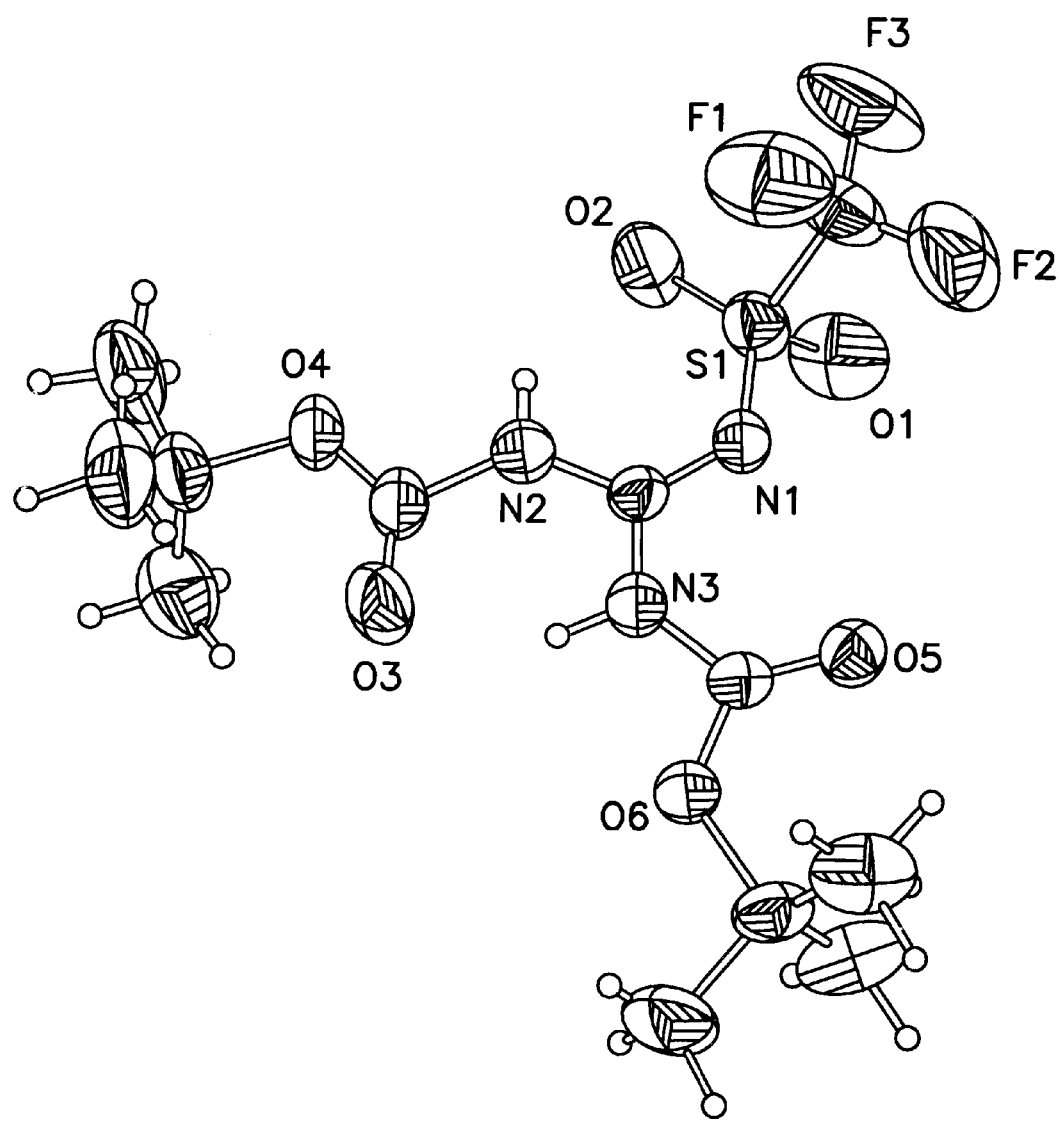
Figure 2:
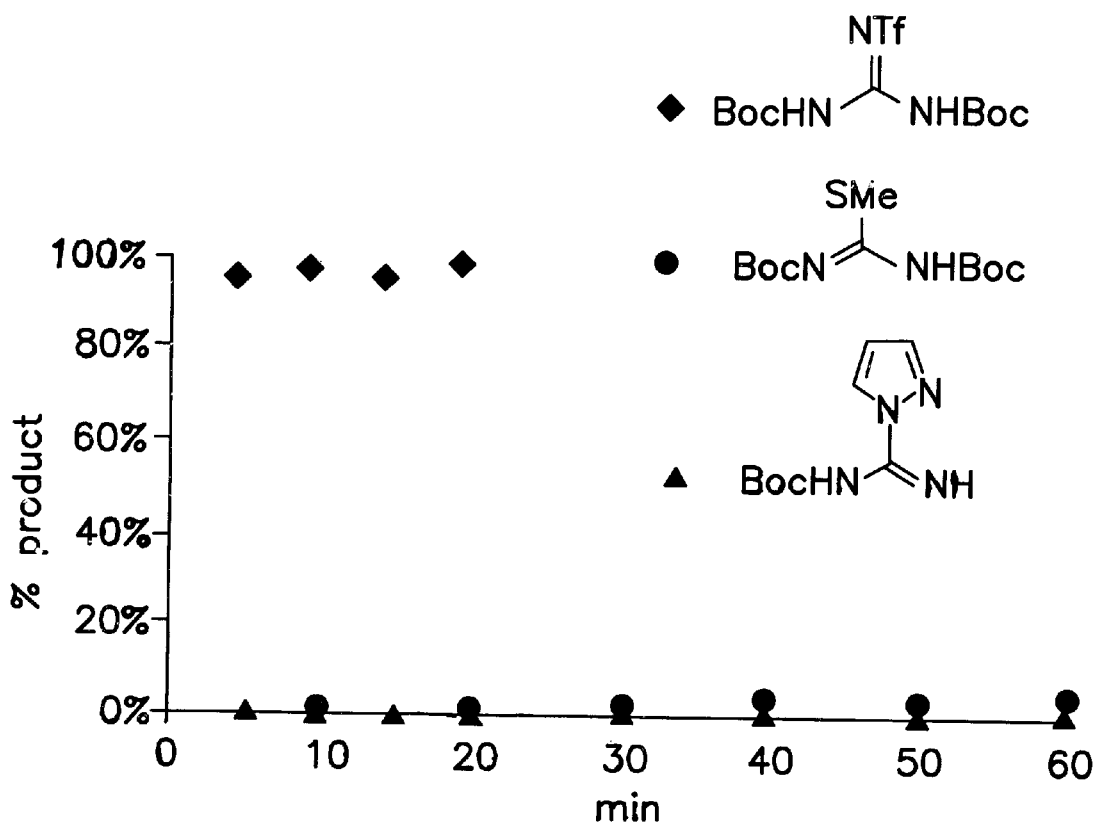
FIG. 2: Comparison of N-,N'-di-Boc-N"-triflyl-guanidine with two commercially available guanidinylation reagents. All three reactions were carried out in an NMR-instrument and the formation of product was followed by integration of the signals of the benzylic $CH_2$-groups. In all reactions the concentration of the guanidinylating agent was 100 mM and the concentration of benzyl amine was 90 mM. Benzene-d6 was used as a solvent. Similar results were obtained in deuterated chloroform and in deuterated acetonitrile.

The term "alkyl" used herein refers to a monovalent straight or branched chain radical of from one to ten carbon atoms, including, but not limited to methyl, ethyl, n-propyl, isopropyl, n-butyl, isobutyl, tert-butyl, n-hexyl, and the like. Alkyl also represents cyclic radicals, including, but not limited to cyclopropyl, cyclobutyl, cyclopentyl, cyclohexyl, and the like.

The term "perfluoroalkyl" as used herein refers to a monovalent straight chain radical of from one to four carbon atoms, in which all hydrogen atoms are substituted by fluorine. A typical perfluorinated alkyl group is the trifluoromethyl group.

The term "aryl" when used alone refers to an aromatic radical whether or not fused. Preferred aryl groups include phenyl, naphthyl, biphenyl and the like. Aryl also refers to heteroaromatic groups including, but not limited to, furanyl, pyrrolyl, thienyl, pyrazolyl, thiazolyl, oxazolyl, pyridyl, pyrimidinyl, indolyl, and the like.

The term "substituted aryl" denotes an aryl group substituted with one, two or three substituents chosen from halogen, cyano, nitro, C1–C10 alkyl, C1–C10-alkyloxy, trifluoromethyl, alkyloxycarbonyl, and the like. Examples of such groups are 4-chlorophenyl, 2-methylphenyl, and 3-ethoxyphenyl.

The term "arylalkyl" means one, two or three aryl groups having the designated number of carbons, appended to an alkyl chain having the number of carbons designated. A typical arylalkyl group is the benzyl group.

The term "alkenyl" refers to a straight or branched chain group of from two to ten carbon atoms containing a carbon-carbon double bond, including, but not limited to allyl, vinyl, and the like.

Guanidinylation Reagents

We have discovered two types of guanidinylation reagents that allow the synthesis of protected guanidines. Compounds of type I comprise guanidines with three symmetrically arranged electron-withdrawing protecting groups (P) and have the structure

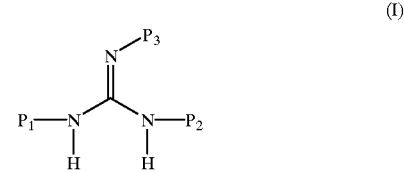

(I)

wherein $P_1$, $P_2$ and $P_3$ are the same or different urethane protecting groups, each having the general structure

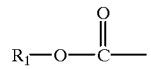

wherein R is a substituted or unsubstituted alkyl or aryl group or heterocyclic group.

P is chosen from urethane protecting groups which are conveniently removable. These groups are available in an almost limitless number. Reviews of urethane groups and their use in peptide synthesis are provided by Geiger, R. and König, W. in "The Peptides" (Gross, E. Meienhofer, J., eds) Vol.3, p3. New York, N.Y. 1981 and in Wünsch, E. Methoden der Org. Chem. (Houben-Weyl) Vol. 15/1 (Wünsch, E.,ed.), p.46, Stuttgart: Thieme 1974. Particularly preferred are the urethane groups containing a substituted or unsubstituted benzylic carbon atom. Urethane-type protecting groups having a benzylic carbon atom are described by Bodanszky, M. (1984) Principles of Peptide Synthesis Chap. III Sec. C, Springer-Verlag, N.Y. 1984. Such groups are removable by hydrogenolysis and by acidolysis, as well as by base-induced β-elimination. Preferably, the protecting group P is an alkyloxylcarbonyl group such as Boc (P=tert-butyloxycarbonyl), Cbz (P=benzyloxycarbonyl), Alloc (P=allyloxycarbonyl), Troc (P=2,2,2-trichloroethyloxycarbonyl), or Moz (P=4-methoxybenzyloxycarbonyl). The protecting groups Boc and Cbz are particularly preferred.

The protected type I guanidines of the invention are weak acids and can be used to guanidinylate primary or secondary alcohols in a Mitsunobu-reaction to produce triprotected alkyl guanidines (scheme 1). The product of such a reaction still possesses one acidic hydrogen atom which can be exploited in a second Mitsunobu-reaction to produce protected dialkylated guanidines.

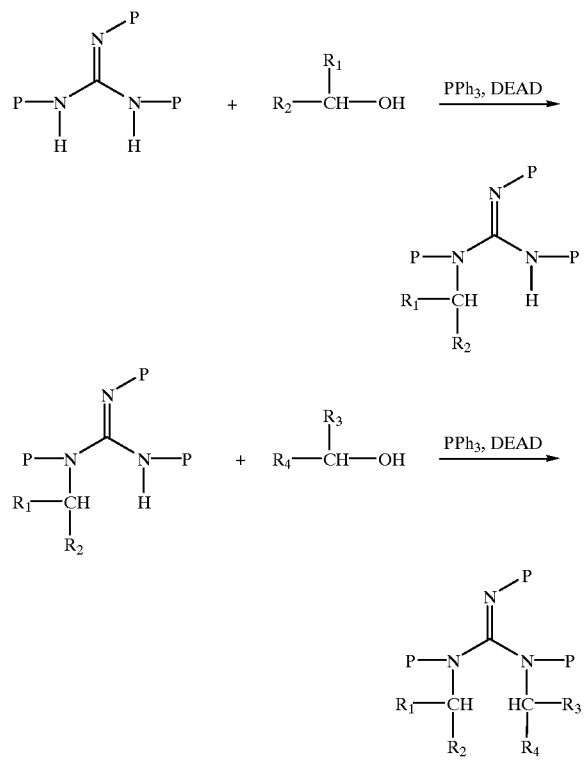

$R_1$, $R_2$, $R_3$, and $R_4$ can be hydrogen or any substituted or unsubstituted alkyl, alkenyl, aryl, or arylalkyl group as described earlier. $R_1$ and $R_2$ (and/or $R_3$ and $R_4$) may be part of a ring structure as in cyclopropanol, cyclobutanol, cyclopentanol, cyclohexanol and the like.

Compounds of type II comprise guanidines with a sulfonyl group in addition to two urethane protecting groups, having the structure (II)

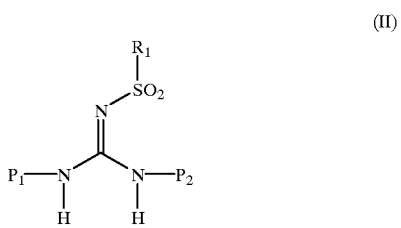

wherein $P_1$ and $P_2$ are as defined above and $R_1$ is a substituted or unsubstituted alkyl or aryl group. Perfluoro-alkyl groups are preferred. Type II protected guanidines react with primary or secondary amines to produce diprotected alkyl guanidines (scheme 2).

Scheme 2
Guanidinylation of amines

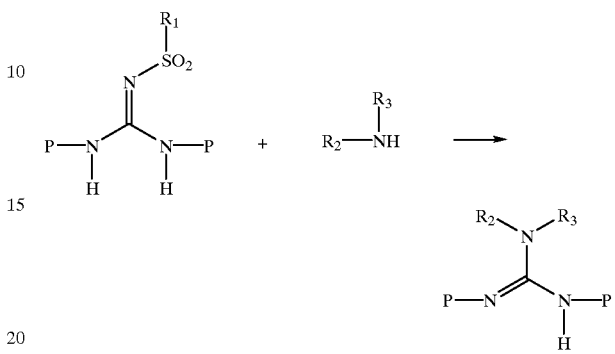

$R_2$ and $R_3$ can be hydrogen or any substituted or unsubstituted alkyl, alkenyl, aryl, or arylalkyl group as described earlier. $R_2$ and $R_3$ may be part of a ring structure as in aziridine, azetidine, pyrrolidine, piperidine, morpholine, and the like.

Preferably, P is Boc or Cbz and $R_1$ is phenyl, 4-methylphenyl, methyl, or trifluoromethyl. Analogs with other protecting groups such as Troc, Alloc or Moz at the P-position are expected to show the same kind of reaction. Because of the exceptionally strong electron-withdrawing character of the triflyl group, the triflyl-guanidines ($R_1$= trifluoromethyl) are the most reactive among the compounds synthesized so far and these are therefore preferred. They have been shown to be superior to previously described guanidinylating reagents.

SYNTHESIS PROCEDURES

Synthesis of Guanidinylation Agents of Type I

A general route towards symmetrical trisubstituted guanidines is shown in scheme 3. The introduction of the first two protecting groups into guanidine hydrochloride is accomplished in one step. Yields between 50 and 80% are usually obtained. The diprotected guanidine is then treated with two equivalents of sodium hydride under anhydrous conditions. Acylation of the resulting anion then completes the synthesis. Preferably, R is benzyl, 2-chlorobenzyl, 4-methoxylbenzyl, 2,2,2-trichloroethyl, allyl, or tert-butyl and X is chloro, azido, succinimidyloxy, or alkoxycarbonyloxy.

Scheme 3
Synthesis of triprotected guanidines

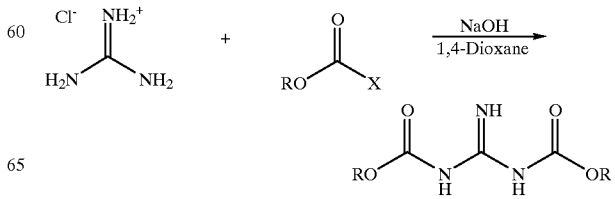

-continued

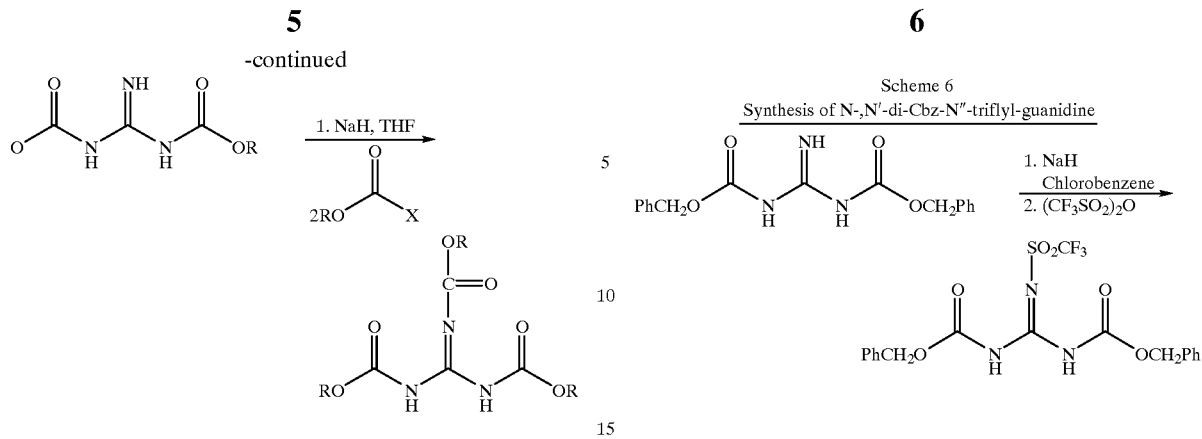

Alternatively, symmetrical triprotected guanidines can be synthesized in one step from guanidine hydrochloride by phase transfer catalysis (scheme 4). Acylating reagents wherein R=benzyl, R=allyl, and R=2,2,2-trichloroethyl are preferred.

Scheme 4
General synthesis of triprotected guanidines by phase transfer catalysis

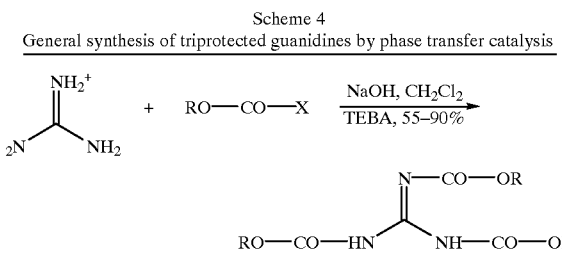

Synthesis of Guanidinylation agents of Type II

Guanidinylation agents of type II can be synthesized by deprotonation of diprotected guanidines with sodium hydride in an inert solvent and reaction of the resulting anion with a sulfonyl chloride (scheme 5). This method was successfully applied in the synthesis of N-,N'-di-Cbz-N''-methylsulfonyl-guanidine ($R_1$=benzyl, $R_2$=Methyl), N-,N'-di-Cbz-N''-phenylsulfonyl-guanidine ($R_1$=benzyl, $R_2$=phenyl), and N-,N'-di-Cbz-N''-tosyl-guanidine ($R_1$=benzyl, $R_2$=tosyl).

Scheme 5
Sulfonylation of diprotected guanidines

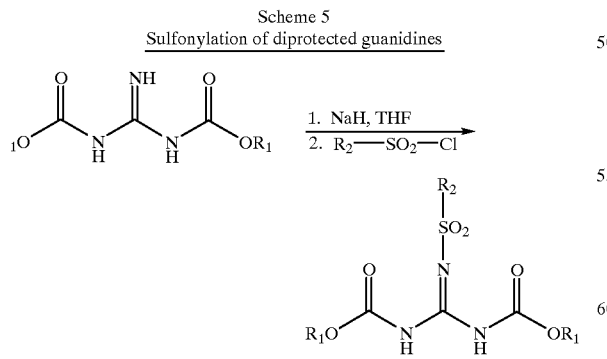

Instead of sulfonyl chlorides, sulfonyl anhydrides can be used as shown in the synthesis of N-,N'-di-Cbz-N''-triflyl-guanidine (scheme 6).

Scheme 6
Synthesis of N-,N'-di-Cbz-N''-triflyl-guanidine

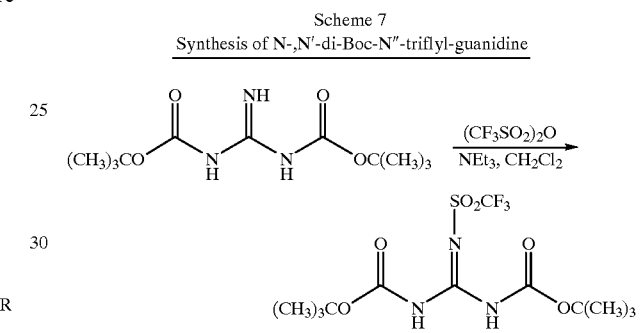

In some cases triethylamine can be used as a base instead of sodium hydride. An example is given in scheme 7 with the synthesis of N-,N'-di-Boc-N''-triflyl-guanidine.

Scheme 7
Synthesis of N-,N'-di-Boc-N''-triflyl-guanidine

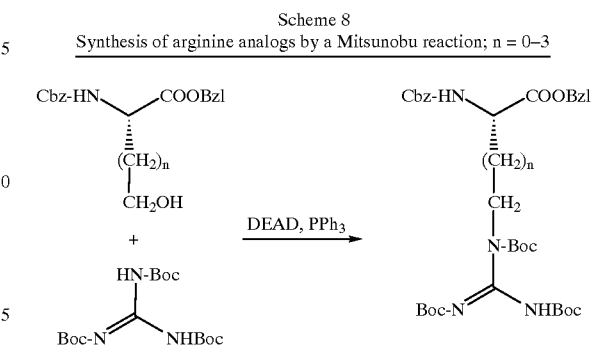

Reactions of Guanidinylation Agents of Type I

Guanidinylation reagents of type I react with primary and secondary alcohols in a Mitsunobu-reaction to produce protected alkylated guanidines. This is exemplified in the synthesis of several orthogonally protected arginine analogs (scheme 8) from suitable precursor molecules. The reactions with N-,N'-,N''-tri-Boc-guanidine are preferably carried out in refluxing THF and yields of up to 70% can be obtained. If N-,N'-,N''-tri-Cbz-guanidine is used as the guanidinylating species, the reaction can be carried out at room temperature. In addition, the yields are usually somewhat higher (up to 86%) than in comparable reactions with N-,N'-,N''-tri-Boc-guanidine.

Scheme 8
Synthesis of arginine analogs by a Mitsunobu reaction; n = 0–3

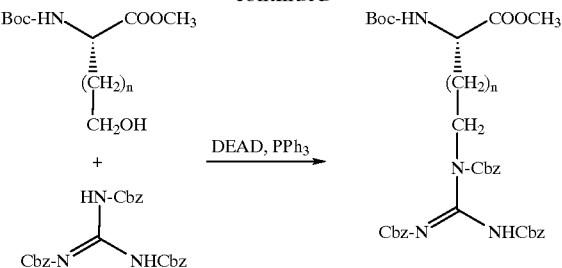

Many biologically interesting guanidines contain two different alkyl substituents connected to two different N-atoms of the guanidine nucleus. Compounds of this type are accessible from triprotected guanidines by two consecutive Mitsunobu-reactions. An example is given in scheme 9 with the synthesis of protected derivative of ω-methyl-arginine, an important inhibitor of nitric oxide synthethase.

Scheme 9
Synthesis of an ω-methyl-arginine derivative by two consecutive Mitsunobu-reactions

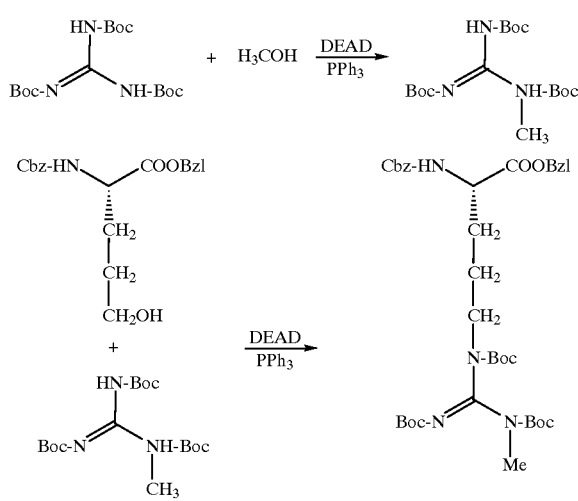

Reactions of Guanidinylation Agents of Type II

N-,N'-Di-Boc-N"-triflyl-guanidine reacts rapidly and under mild conditions with primary (scheme 10) and secondary amines (scheme 11). The reactions are carried out at room temperature and are usually complete within 1 h. Successful guanidinylation reactions have been performed in a wide range of solvents such as benzene, chloroform, or dichloromethane, acetonitrile or DMSO. Unpolar solvents such as benzene, chloroform, or dichloromethane are preferred. Compounds that are insoluble in one of the preferred solvents can in many cases be converted into a more soluble derivative which can then be successfully guanidinylated. This is demonstrated in scheme 10 with the synthesis of a homoarginine derivative from N-α-Fmoc-lysine. In this procedure N-α-Fmoc-lysine is first silylated with MSTFA (N-methyl-N-trimethylsilyltrifluoroacetamide) to generate a derivative that is soluble in dichloromethane. This derivative is then guanidinylated in the same pot with N-,N'-di-Boc-N"-triflyl-guanidine. The silyl-groups used to solubilize the starting material are removed again during the workup procedure. Other protected diamino acids such as N-α-Fmoc-ornithine, N-α-Fmoc-2,4-diamino-butyric acid or N-α-Fmoc-2,3-diamino-propionic acid are expected to show the same kind of reaction. The arginine analogues produced by this methodology are orthogonally protected and can be used for peptide coupling reactions without further modifications.

Scheme 10
Reaction of N-,N'-di-Boc-N"-triflyl-guanidine Fmoc-Lys

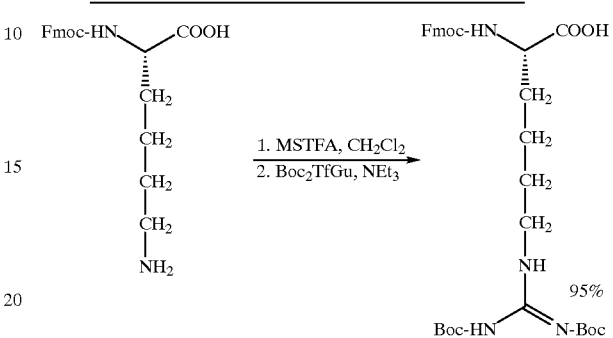

Exceptionally good yields of protected guanidines are obtained by guanidinylation of secondary amines (scheme 11). Even with divalent amines such as piperazine the reaction is extremely facile.

Scheme 11
Reaction of N-,N'-di-Boc-N"-triflyl-guanidine with secondary amines

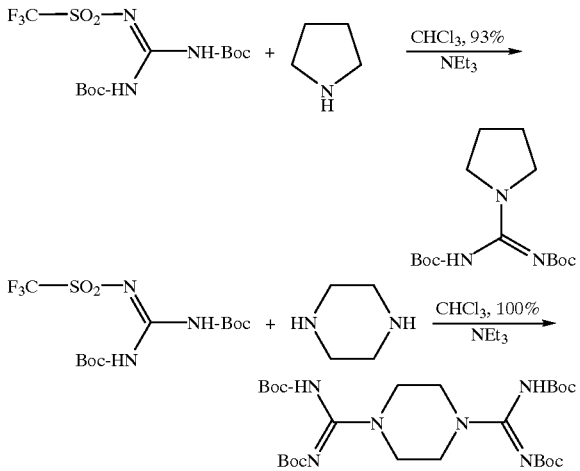

N-,N'-Di-Cbz-N"-triflyl-guanidine is an excellent reagent for the guanidinylation of unreactive aromatic amines. The reaction with aniline is complete after 1 h at room temperature (scheme 12).

Scheme 12
Reaction of N-,N'-di-Cbz-N"-triflyl-guanidine with aniline

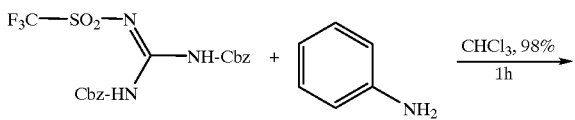

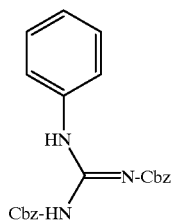

Guanidinylations with N-,N'-Di-Boc-N"-triflyl-guanidine on Solid Phase

Reactions on solid phase are usually slower than comparable reactions in solution. Much effort is currently directed to adapt useful chemical reactions to the unique conditions of solid phase synthesis. Such optimized reactions are especially important for the construction of chemical libraries by parallel and combinatorial methods.

The high reactivity of N-,N'-di-Boc-N"-triflyl-guanidine allows guanidinylations on solid phase to be performed successfully. This is demonstrated by the conversion of an ornithine residue in a peptide sequence to arginine (scheme 13). The peptide was assembled on a PAM-resin (PAM: phenylacetamidomethyl) by standard methods. Ornithine, the ε-amino group protected by Fmoc, was incorporated in place of arginine. After complete assembly of the sequence the Fmoc-group on the ornithine side chain was removed selectively and the free amino group was guanidinylated with N-,N'-di-Boc-N"-triflyl-guanidine. The unprotected arginine-containing peptide was then obtained after removal of the Boc-groups and cleavage of the peptide from the resin with HF. Analysis of the crude peptide by FAB-MS indicated a homogeneous product. No peaks suggesting incomplete guanidinylation could be detected.

The strategy as outlined in scheme 13 could prove to be very valuable for synthesis of peptides containing multiple arginine residues. Such peptides are often difficult to synthesize by conventional methods.

Scheme 13
Synthesis of arginine-containing peptides by conversion of ornithine to arginine on solid phase

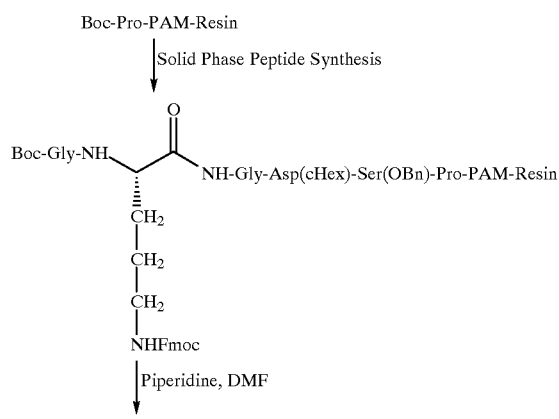

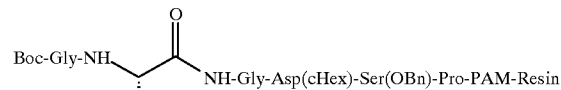

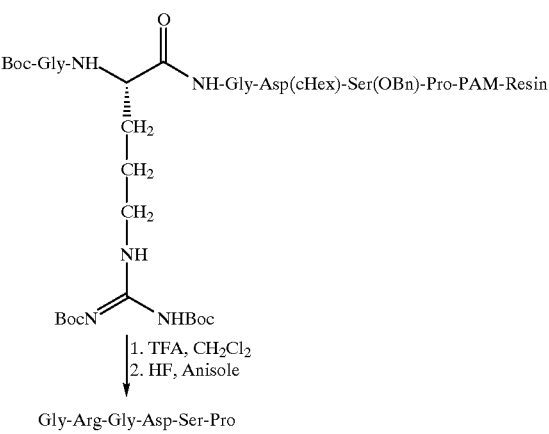

Comparison of N-,N'-Di-Boc-N'-triflyl-guanidine with Other Guanidinylating Reagents The guanidinylation of benzylamine in benzene was chosen as a model reaction to compare two commercially available guanidinylating agents with N-,N'-di-Boc-N"-triflyl-guanidine (scheme 14). All three reactions were carried out in an NMR-instrument and the formation of product was followed by integration of the signals of the benzylic $CH_2$-groups. Under the conditions chosen, N-,N'-di-Boc-N"-triflyl-guanidine proved superior to the other reagents. Similar results were obtained in deuterated chloroform and ind deuterated acetonitrile.

Scheme 14
Guanidinylation of Benzylamine

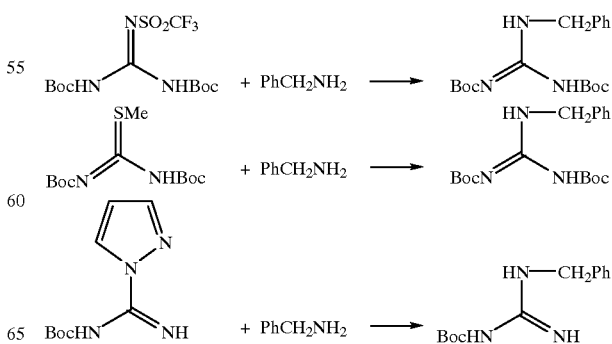

EXPERIMENTAL PROCEDURES

Example 1

N-,N'-,N"-Tri-Boc-guanidine

Potassium hydroxide pellets (2.81 g, 50 mmol) and sodium carbonate (5.30 g, 50 mmol) are finely ground in a mortar and transferred into a 250 ml round bottomed flask equipped with a magnetic stirrer and a reflux condenser. DMSO (50 ml) is added and the resulting suspension is stirred for 5 min at room temperature. Guanidine hydrochloride (4.78 g, 50 mmol) is added and the mixture is again stirred for 5 min After the addition of di-tert-butyl-dicarbonate (51.7 ml, 225 mmol) the mixture is stirred for 60 h at 40° C. The colorless precipitate obtained by pouring the cold reaction mixture into 1 l water is collected by filtration on Buechner funnel, washed with water and dried overnight in vacuo. Recrystallization from acetonitrile yields colorless needles (14.9 g , 83%): mp 147–150° C. (dec); $^1$H NMR (360 MHz, CDCl$_3$) δ 1.48 (s, 27H); FAB-MS m/e (relative intensity) 360 (100, M+H$^+$), 304 (34), 260 (10), 248 (74); Anal. Calc. for: C, 53.47%; H, 8.13%;.N, 11.69%; Found: C, 53.48%; H, 8.34%;.N, 11.86%.

Example 2

N-,N'-,N"-Tri-Cbz-guanidine

Sodium hydride (400 mg, 60% dispersion in mineral oil) is added in small portions to a suspension of N-,N'-di-Cbz-guanidine (1.65 g, 5.0 mmol) in anhydrous THF (20 ml) at −45° C. under an atmosphere of argon. After the addition is completed, the mixture is stirred for 1 h at −45° C. Benzyl chloroformate (0.82 ml, 5 mmol) is added, the mixture is allowed to warm up to room temperature and stirred overnight. The solvent is removed under reduced pressure and the residue is dissolved in a mixture of dichloromethane (50 ml) and water (25 ml). The phases are separated and the aqueous layer is extracted twice with dichloro methane (50 ml each). The extracts are combined, washed with 1N hydrochloric acid and water and dried with magnesium sulfate. After filtering and removal of the solvent under reduced pressure the crude product is purified by flash chromatography on silica gel (eluent: dichloromethane-ethyl ether 98:2). N-,N'-N"-tri-Cbz-guanidine (2.07 g, 90%) is obtained as a white powder: mp: 111–112° C.; $^1$H NMR (360 MHz, DMSO-d$_6$) δ 10.55, (s, 2H), 7.36 (s, 10H), 5.22 (br s, 6H); FAB-MS m/e (relative intensity) 506 (5, M−H$^+$+2Na$^+$), 484 (100, M+Na$^+$), 462 (24, M+H$^+$); Anal. Calc. for C, 65.07%; H, 5.02%;.N, 9.11%; Found: C, 64.89%; H, 4.74%;.N, 8.82%.

Example 3

N-Methyl-N-,N'-,N"-Tri-Boc-Guanidine

A solution of anhydrous methanol (0.04 ml, 1.0 mmol), N-,N'-,N"-tri-Boc-guanidine (1.80 g, 5.0 mmol), and triphenylphoshine (393 mg, 1.5 mmol) in anhydrous THF (50 ml) is cooled to −5° C. under an atmosphere of argon. Diethylazodicarboxylate (DEAD, 0.22 ml, 1.5 mmol) is added dropwise at a rate such that the reaction mixture is completely colorless before addition of the next drop. After the addition is completed, the reaction mixture is refluxed for 15 h. The solution is then cooled to room temperature, and hexanes (50 ml) is added. A precipitate of excess N-,N'-,N"-tri-Boc-guanidine forms which is collected by filtration on a Buechner-funnel and washed with a mixture of THF/hexanes 1:1. The filtrate is concentrated under reduced pressure and the product (colorless oil, 182 mg, 49%) isolated by flash chromatography on silica gel (eluent: dichloromethane-ethyl ether 98:2): $^1$H NMR (360 MHz, DMSO-d$_6$) δ 10.17 (s, 1H), 2.94 (s, 3H), 1.43–1.36 (27H); FAB-MS m/e (relative intensity).

Example 4

L-N-Cbz-δ,ω,ω'-Tri-Boc-Arginine Methyl Ester

A solution of S-N-Cbz-2-amino-5-hydroxy-valeric acid methyl ester (0.56 g, 2.0 mmol), N-,N'-,N"-tri-Boc-guanidine (3.59 g, 10.0 mmol), and triphenylphoshine (0.79 g, 3.0 mmol) in anhydrous THF (100 ml) is cooled to −5° C. under an atmosphere of argon. Diethylazodicarboxylate (DEAD, 0.45 ml, 3.0 mmol) is added dropwise at a rate such that the reaction mixture is completely colorless before addition of the next drop. After the addition is completed, the reaction mixture is stirred for 18 h at 45° C. The solution is then cooled to room temperature, and hexanes (100 ml) is added. A precipitate of excess N-,N'-N"-tri-Boc-guanidine forms which is collected by filtration on a Buechner-funnel and washed with a mixture of THF/hexanes 1:1. The filtrate is concentrated under reduced pressure and the product (colorless oil, 0.87 g, 70%) isolated by flash chromatography on silica gel (eluent: dichloromethane-ethyl ether 9:1): $^1$H NMR (360 MHz, DMSO-d$_6$) δ 10.18 (s, 1H), 7.72 (d, 1H, J=7.9 Hz), 7.40–7.26 (m, 5H), 5.01 (s, 2H), 4.03–3.94 (m, 1H), 3.60 (s, 3H), 3.45 (t, 2H, J=5.8 Hz), 1.73–1.45 (m, 4H), 1.39 (s, 18H), 1.37 (s, 9H); FAB-MS m/e 623 (M+H$^+$).

Example 5

L-N-Cbz-ω-Methyl-δ,ω,ω'-Tri-Boc-Arginine Benzyl Ester

A solution of S-N-Cbz-2-amino-5-hydroxy-valeric acid methyl ester (143 mg, 0.4 mmol), N-methyl-N-,N'-,N"-tri-Boc-guanidine (150 mg, 0.4 mmol), and triphenylphoshine (105 mg, 0.4 mmol) in anhydrous THF (2 ml) is cooled to −5° C. Diethylazodicarboxylate (DEAD, 0.06 ml, 0.38 mmol) is added dropwise at a rate such that the reaction mixture is completely colorless before addition of the next drop. After the addition is completed, the reaction mixture is refluxed for 3 h. The solvent is removed under reduced pressure and the product (colorless oil, 181 mg, 63%) is isolated by flash chromatography on silica gel (eluent: ethyl acetate-hexanes 1:3): $^1$H NMR (360 MHz, DMSO-d$_6$) δ 7.80 (d, 2H, J=7.9 Hz), 7.39–7.28 (m, 10H), 5.10 (s, 2H), 5.06–4.94 (m, 2H), 4.11–4.00 (m, 1H), 3.53–3.44 (m, 2H), 2.89 (s, 3H), 1.75–1.50 (m, 4H), 1.40–1.34 (27H); FAB-MS ?m/e 845 (M+Cs$^+$).

Example 6

N-,N'-Di-Boc-Guanidine 1,4-Dioxane (50 ml) is added to a solution of guanidine hydrochloride (2.39 g, 25 mmol) and sodium hydroxide (4.0 g, 0.1 mol) in water (25 ml) and the resulting mixture is cooled to 0° C. Di-tert-butyl-pyrocarbonate(12.0 g, 55 mmol) is added in one portion while stirring. The reaction mixture is allowed to warm to room temperature within 2 h. After stirring for 20 h the mixture is concentrated in vacuo to one third of its original volume. The resulting suspension is diluted with water (50 ml) and extracted three times with ethyl acetate (50 ml each). The combined extracts are washed with 10% citric acid, water and brine and dried with magnesium sulfate. After filtering and removal of the solvent under reduced pressure the crude product is purified by flash chromatography on silica gel (eluent: dichloromethane-methanol 97:3). N-,N'-di-Boc-guanidine (3.84 g, 59%) is obtained as a colorless powder: mp: 144° C.; $^1$H NMR (360 MHz, DMSO-d$_6$) δ 10.42 (br s, 1H), 8.47 (br s, 2H), 1.39 (s, 18H); FAB-MS m/e (relative intensity) 260 (50, M+H$^+$), 204 (48), 148 (100); Anal. Calc. for: C, 50.95%; H, 8.16%;.N, 16.21%; Found: C, 50.83%; H, 8.04%;.N, 16.26%.

Example 7

N-N'-Di-Boc-N"-Trifluoromethanesulfonyl-Guanidine

A solution of N-,N'-di-Boc-guanidine (0.52 g, 2.0 mmol) and triethyl amine (0.29 ml) in anhydrous dichloromethane (10 ml) is cooled to −78° C. under an atmosphere of argon. Triflic anhydride (0.35 ml, 2.1 mmol) is added dropwise at a rate such that reaction temperature does not exceed −65° C. After the addition is completed, the mixture is allowed to warm to room temperature within 4 h. The solution is transferred to a separation funnel, washed with 2M sodium bisulfate and water and dried with anhydrous sodium sulfate. After filtering and removal of the solvent under reduced pressure the crude product is purified by flash chromatography on silica gel (eluent: dichloromethane). N-N'-di-Boc-N"-trifluoromethanesulfonyl-guanidine (686 mg, 88%) is obtained as pale yellow crystals. The product can be further purified by recrystallization from hexanes: mp: 115° C.; $^1$H NMR (360 MHz, DMSO-d$_6$) δ 11.45 (br s, 2H), 1.45 (s, 18H). FAB-MS m/e (relative intensity) 414 (16, M+Na$^+$), 392 (13, M+H$^+$), 336 (43), 280 (100), 236 (9); Anal. Calc. for C, 36.83%; H, 5.15%;.N, 10.74%; F, 14.56%; S, 8.19%; Found: C, 36.93%; H, 5.21%;.N, 10.66%; F, 14.80%; S, 8.33%.

Example 8

N-,N'- Di-Cbz-Guanidine

Dichloromethane (80 ml) is added to a solution of guanidine hydrochloride (3.82 g, 40 mmol) and sodium hydroxide (8 g, 0.2 mol) in water (40 ml) and the resulting mixture is cooled to 0° C. Benzyloxycarbonyl chloride (17.1 ml, 120 mmol) is added dropwise with vigorous stirring over a period of 45 min. After the addition is completed, stirring is continued for 20 h at 0° C. The mixture is diluted with dichloromethane (100 ml), the layers are separated and the aqueous layer is extracted with dichloromethane (100 ml). The extracts are combined, washed with water and dried with magnesium sulfate. After filtering and removal of the solvent under reduced pressure the crude product is recrystallized from methanol. N-,N'-Di-Cbz-guanidine (9.85 g, 75%) is obtained as colorless crystals: mp: 149–150° C.; $^1$H NMR (360 MHz, DMSO-d$_6$) δ 10.88 (br s, 1H), 8.67 (br s, 2H), 7.40–7.25 (m, 10H), 5.10 (s, 4H); Anal. Calc. for C, 62.38%; H, 5.23%;.N, 12.84%. Found: C, 62.26%; H, 5.01%;.N, 12.79%.

Example 9

N-N'-Di-Cbz-N"-Trifluoromethanesulfonyl-Guanidine

Sodium hydride (400 mg, 60% dispersion in mineral oil) is added to a solution of N-,N'-di-Cbz-guanidine (1.65 g, 5.0 mmol) in anhydrous chlorobenzene (50 ml) at 0° C. under an atmosphere of argon. After stirring for 1 h at 0° C., the mixture is cooled to −45° C. Triflic anhydride (0.82 ml, 5 mmol) is added, the mixture is allowed to warm up to room temperature and stirred overnight. The solvent is removed under reduced pressure and the residue is dissolved in a mixture of ethyl acetate (100 ml) and 2M sodium bisulfate (25 ml). The phases are separated and the organic layer is washed with water and brine and dried with magnesium sulfate. After filtering and removal of the solvent under reduced pressure the crude product is purified by flash chromatography on silica gel (eluent: dichloromethane-ethyl ether 95:5). N-N'-di-Cbz-N"-trifluoromethanesulfonyl-guanidine (1.58 g, 69%) is obtained as a pale oil that crystallizes in vacuo: mp: 74–75° C.; $^1$H NMR (360 MHz, DMSO-d$_6$) δ 11.55 (br s, 2H), 7.45–7.28 (m, 10H), 5.20 (s, 4H); Electrospray-MS m/e (relative intensity) 498 (30, M+K$^+$), 482 (100, M+Na$^+$), 460 (2, M+H$^+$); Anal. Calc. for C, 47.06%; H, 3.51%;.N, 9.15%; F, 12.41%; S, 6.98%; Found: C, 47.37%; H, 3.35%;.N, 8.67%; F, 12.79%; S, 6.92%.

Example 10

N-Cbz-Guanidine 1,4-Dioxane (20 ml) is added to a solution of guanidine hydrochloride (0.96 g, 10 mmol) and sodium hydroxide (0.8 g, 20 mmol) in water (10 ml) and the resulting mixture is cooled to 0° C. Benzyloxycarbonyl chloride (1.1 ml, 7.7 mmol) is added dropwise with vigorous stirring over a period of 10 min. After the addition is completed, the ice-bath is removed and stirring is continued for 1 h at room temperature. The mixture is concentrated in vacuo to one third of its original volume and extracted three times with ethyl acetate (20 ml each). The combined extracts are washed with brine (20 ml) and dried with anhydrous sodium sulfate. After filtering and removal of the solvent under reduced pressure N-Cbz-guanidine (1.31 g, 88%) is obtained as a white powder: mp: 120–122° C.; $^1$H NMR (360 MHz, DMSO-d$_6$) δ 7.35–7.25 (m, 5H), 6.88 (br s, 4H), 4.95 (s, 2H); Electrospray-MS m/e 194 (M+H$^+$).

Example 11

N-Boc-N'-Cbz-Guanidine

A solution of di-tertbutyl-pyrocarbonate (1.32 g, 6.05 mmol) in acetone (5 ml) is added in one portion to a stirred solution of N-Cbz-guanidine (1.30 g, 6.73 mmol) and triethyl amine (0.94 ml) in acetone (15 ml). After stirring for 48 h at room temperature the solvent is removed under reduced pressure and the resulting residue is dissolved in a mixture of ethyl acetate (100 ml) and water (50 ml). The phases are separated and the organic layer is washed with 2M sodium bisulfate, water and brine and dried with anhydrous sodium sulfate. After filtering and removal of the solvent under reduced pressure the crude product is purified by flash chromatography on silica gel (eluent: dichloromethane-ethyl ether 9:1). N-Boc-N'-Cbz-guanidine (1.44 g, 82%) is obtained as a white powder: mp: 125–126° C.; $^1$H NMR (360 MHz, DMSO-d$_6$) δ 10.59 (br s, 1H), 8.69 (br s, 1H), 8.50 (br s, 1H), 7.40–7.25 (m, 5H), 5.04 (s, 2H), 1.42 (s, 9H).

Example 12

N-tert-Butoxycarbonyl-N'-Cbz-N"-Trifluorometbanesulfonyl-Guanidine

A solution of N-Boc-N'-Cbz-guanidine (586 mg, 2.0 mmol) and triethyl amine (0.42 ml) in anhydrous dichloromethane (20 ml) is cooled to −78° C. under an atmosphere of argon. Triflic anhydride (0.42 ml, 2.5 mmol) is added dropwise at rate such that reaction temperature does not exceed −65° C. After the addition is completed, the mixture is allowed to warm to room temperature within 4 h. The solution is transferred to a separation funnel, washed with 2M sodium bisulfate and water and dried with anhydrous sodium sulfate. After filtering and removal of the solvent under reduced pressure the crude product is purified by flash chromatography on silica gel (eluent: dichloromethane). N-Boc-N'-Cbz-N"-trifluoromethanesulfonyl-guanidine (699 mg, 82%) is obtained as a pale oil that crystallizes upon drying in vacuo: mp: 95–97° C.; $^1$H NMR (360 MHz, DMSO-d$_6$) δ 11.49 (br s, 1H), 11.17 (br s, 1H), 7.40 (m, 5H), 5.21 (s, 1H), 1.43 (s, 9H); FAB-MS m/e (relative intensity) 448 (23, M+Na$^+$), 426 (44, M+H$^+$), 329 (5), 370 (100), 348 (15), 326 (15).

Example 13

N,N'-Bis(tert-Butyloxycarbonyl)-Pyrrolidine-1-Carboxamidine

N-N'-Di-Boc-N"-trifluoromethanesulfonyl-guanidine (235 mg, 0.6 mmol) is added to a solution of pyrrolidine (0.042 ml, 0.5 mmol) and triethyl amine (0.083 ml) in chloroform (1 ml). After stirring for 4 h at room temperature, the product is isolated by flash chromatography on silica gel (eluent: ethyl acetate-hexane 2:3). The product (146 mg, 93%) is obtained as a colorless oil that crystallizes in vacuo: mp: 88–91° C.; $^1$H NMR (360 MHz, CDCl$_3$) δ 3.58–3.53 (m, 4H), 1.90–1.83 (m, 4H), 1.46 (s, 18H); FAB-MS m/e (relative intensity) 649 (13, 2M+Na$^+$), 627 (5, 2M+H+), 336 (29, M+Na$^+$), 314 (100, M+H$^+$), 258 (28), 202 (94).

Example 14

N-N'-Di-Boc-N"-Phenyl-Gunnidine

Aniline (0.055 ml, 0.6 mmol) is added to a solution of N-N'-di-Cbz-N"-trifluoromethanesulfonyl-guanidine in chloroform and the mixture is stirred for 1 h at room temperature. The solvent is removed under reduced pressure the residue is dissolved in ethyl ether (10 ml). The solution is washed with 10% citric acid, water and brine, and dried with magnesium sulfate. After filtration and removal of the solvent under reduced pressure N-N'-di-Boc-N"-phenyl-guanidine (198 mg, 98%) is obtained as a colorless oil. that crystallizes upon drying in vacuo: mp: 105–108° C.; $^1$H NMR (360 MHz, DMSO-d$_6$) δ 11.34 (br s, 1H), 9.99 (s, 1H), 7.56–7.11 (m, 15H), 5.23 (s, 2H), 5.02(s, 1H). FAB-MS m/e (relative intensity) 426 (M+Na$^+$), 404 (M+H$^+$).

The procedures of the invention as described above are to be understood as exemplary and do not indicate limitations of the invention, which is to be understood as limited only by the scope of the following claims.

What is claimed is:

1. A method for solid phase synthesis of a peptide comprising one or more arginine homologs, comprising the steps of:

(a) assembling a sequence (Xaa)$_n$ of amino acids on a solid phase peptide synthesis resin, where Xaa denotes any appropriately protected amino acid and n denotes an integer;

(b) attaching an amino acid having the structure

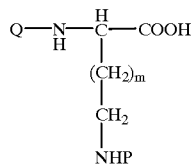

wherein Q is Boc or Fmoc and P is any protecting group that can be selectively removed, and n=0–3, to the amino terminus of the product of step (a);

(c) coupling any sequence of suitably protected amino acids to the amino terminus of the product of step (b);

(d) selectively removing all the protecting groups P as defined in (b) from the product of step (c);

(e) reacting a protected guanidine having the structure

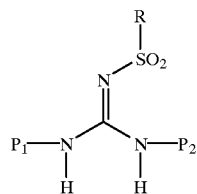

wherein P1 and P2 are the same or different urethane protecting groups, and R is a substituted or unsubstituted alkyl or aryl group or a heterocyclic group, with the product of step (d) to guanidinylate all unprotected amino functions present; and (f) removing all protecting groups and cleaving the peptide from the resin to yield the product

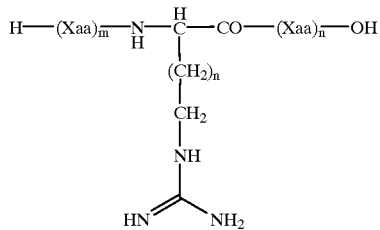

wherein m denotes an integer.

2. The method of claim 1 wherein the sulfonyl guanidinylating group has the structure:

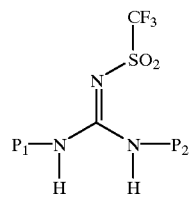

3. The method of claim 1 wherein the sulfonyl guanidinylating group is N-N'-di-Boc-N"-trifluoromethmesulfonyl-guanidine.

4. The method of claim 1 wherein the sulfonyl guanidinylating group is N-N'-di-Cbz-N"-trifluoromethmesulfonyl-guanidine.

5. The method of claim 1 wherein the sulfonyl guanidinylating group is N-Boc-N'-Cbz-N"-trifluoromethmesulfonyl-guanidine.

6. The method of claim 1, wherein P1 and P2 in the sulfonyl guanidinylating group are alkyloxycarbonyl groups.

7. The method of claim 1, wherein P1 and P2 in the sulfonyl guanidinylating group are independently selected from the group consisting of tert-butyloxycarbonyl, benzyloxycarbonyl, allyloxycarbonyl, 2,2,2-trichloroethyloxycarbonyl, and 4-methoxybenzyloxycarbonyl.

8. The method of claim 2, wherein P1 and P2 in the sulfonyl guanidinylating group are alkyloxycarbonyl groups.

9. The method of claim 2, wherein P1 and P2 in the sulfonyl guanidinylating group are independently selected from the group consisting of tert-butyloxycarbonyl, benzyloxycarbonyl, allyloxycarbonyl, 2,2,2-trichloroethyloxycarbonyl, and 4-methoxybenzyloxycarbonyl.

* * * * *